(12) United States Patent
Biesel et al.

(10) Patent No.: US 6,200,276 B1
(45) Date of Patent: Mar. 13, 2001

(54) BLOOD COLLECTING DEVICE

(75) Inventors: Wolfgang Biesel, Ottweiler; Friedrich Witthaus, St. Wendel, both of (DE)

(73) Assignee: Fresenius AG, Bad Homburg (DE)

( * ) Notice: Subject to any disclaimer, the term of this patent is extended or adjusted under 35 U.S.C. 154(b) by 0 days.

(21) Appl. No.: 09/350,017

(22) Filed: Jul. 9, 1999

(51) Int. Cl.[7] .............................. A61B 5/00; B65D 81/00
(52) U.S. Cl. ............................................................. 600/573
(58) Field of Search .................................... 600/573, 580, 600/583; 604/408

(56) References Cited

U.S. PATENT DOCUMENTS

| 4,772,256 | * | 9/1988 | Lane et al. | 600/580 |
| 4,775,360 | * | 10/1988 | Lane et al. | 600/580 |
| 4,857,042 | * | 8/1989 | Schneider | 600/580 |
| 4,976,707 | * | 12/1990 | Bodicky et al. | 604/408 |
| 5,223,228 | | 6/1993 | Telang et al. | |
| 5,354,262 | | 10/1994 | Boehringer et al. | |
| 5,800,779 | * | 9/1998 | Johnson | 600/573 |
| 5,997,519 | * | 12/1999 | Hemstreet et al. | 600/573 |

FOREIGN PATENT DOCUMENTS

| 198 02 351 | 8/1999 | (DE) . |
| 351 980 | 1/1990 | (EP) . |
| 669 139 | 8/1995 | (EP) . |
| WO 97/14450 | 4/1997 | (WO) . |
| WO 98/17369 | 4/1998 | (WO) . |

* cited by examiner

*Primary Examiner*—Max Hindenburg
*Assistant Examiner*—Brian Szmal
(74) *Attorney, Agent, or Firm*—Kenyon & Kenyon

(57) ABSTRACT

The present invention relates to a blood collecting device having a vacuum container and a cover which seals it. A blood filter is provided on the cover. According to the invention, the blood filter has a filter bottom which is designed to be flexible and/or is mounted movably.

5 Claims, 2 Drawing Sheets

Stand der Technik

Stand der Technik

BLOOD COLLECTING DEVICE

This invention relates to a blood collecting device according to the definition of the species of claim 1.

In surgery there is often a great deal of blood at the operation site, which was previously often removed only by suction and then discarded. However, since this blood can be very valuable as a supplemental supply from the standpoint of supplying the patient with donor blood, there have already been numerous proposals for collecting this blood and reprocessing it so that it can be resupplied to the patient.

For example, European Patent 669,139 A has already disclosed a generic blood collecting device in which a partial vacuum is produced so that a blood mixture can be collected by suction from an operation site. This blood is usually contaminated with blood clots, tissue particles, tissue fibers and the like and is more or less extensively diluted and also mixed with anticoagulants. Particulate impurities are filtered out, and the remaining blood is administered to the patient in the form of a transfusion.

Figure 1:
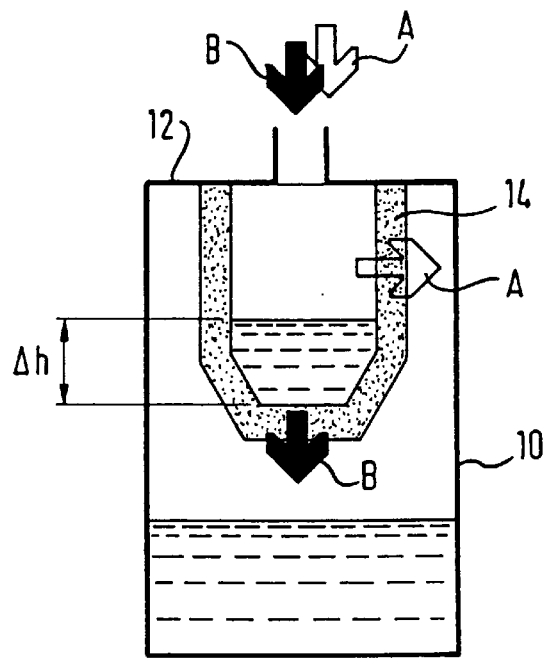
Figure 2:
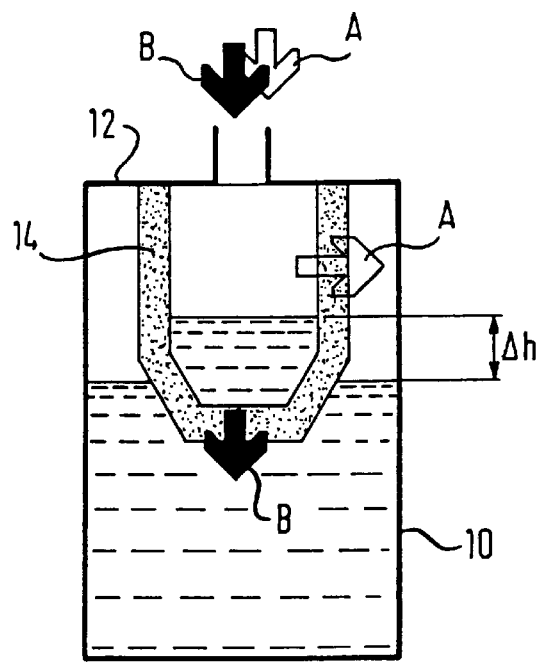

The design of the known blood collecting device according to European Patent 669,139 A is shown schematically in FIGS. 1 and 2. The vacuum container, not shown in detail, of the blood collecting device has an inner bag 10, which is fixedly connected to a cover 12. A rigid filter screen 14 is also connected to the cover 12. The filter screen 14 projects into the bag 10, as shown in FIGS. 1 and 2. A vacuum is created between bag 10 and the vacuum container (not shown in detail here), causing the bag to expand and draw in blood. A drain tube for the filtered blood mixture is arranged between bag 10 and filter 14 in a manner not shown in detail here.

One disadvantage of the known blood collecting device is that the filter projects into the bag. Because of the bag-like construction of the filter, the liquid flow is separated from the air flow on entering the blood collecting device and is conveyed separately through the filter, as indicated by arrow A for air and arrow B for the blood mixture in FIGS. 1 and 2.

Blood drips into filter bag 14, whereas the air flow passes the filter at the side. The pressure difference driving the blood through the filter is created by the filling level of the blood in filter bag 14, i.e., by the hydrostatic pressure of the liquid column on the filter. When the filter bag is immersed, the pressure is created by the geodetic difference in height between the filling levels inside and outside the filter, as illustrated in FIG. 2. The driving pressure difference is typically a maximum of 0.015 bar, i.e., approximately 15 cm liquid column. The filter bag thus empties slowly and not at all if the filter is wetted with clots, for example. In the filter bag, the blood remains in contact for a long time with more solid waste products such as tissue fragments which have a coagulation activating effect. This can lead to blockage of the filter due to additional clotting. Blood is then retained by the filter and cannot be removed from the reservoir.

Other blood collecting containers without any internal bag are also known. At the top, these rigid containers have a blood mixture inlet and an air exhaust. However, the blood outlet may be located in the cover or on the bottom. If it is located in the cover, a drain line leads from the bottom to the cover. If the outlet is at the bottom, the blood mixture runs out of the container by gravity.

However, an embodiment with an internal flexible bag is preferred, because only the internal flexible bag is replaced after the blood collection is completed, so the disposable part is inexpensive.

The object of the present invention is to improve upon a generic blood collecting device, to prevent blockage and clogging of the filter and also increase the recovery of blood cells.

According to the present invention, this object is achieved against the background of a generic blood collecting device through the additional characterizing features of claim 1.

The blood filter is designed in the form of a filter chamber in the cover or directly adjoining it. According to the present invention, only the bottom of the filter chamber is designed as a filter, with this filter being bordered at the edges and not supported. This gives the filter surface a certain flexibility in the direction of flow. Surprisingly, a reduction in flow or obstruction is completely prevented due to this increased flexibility, which can be explained by the displacement and shifting of the retained group material because of the movement of the filter.

In addition, due to the fact that the filter is no longer designed as a bag projecting into the blood reservoir, this prevents the air flow from carrying the blood to be filtered through the filter along a separate path. The blood filter is now designed so that the air flow runs parallel to the liquid flow through the filter surface of the blood filter. Thus, the air flow produced by the partial vacuum is the driving force for filtration. The maximum pressure difference driving the blood through the filter with this blood collecting device according to this invention is on the order of the vacuum pressure which is approximately 0.1 bar. Consequently, the blood has only a very short dwell time inside the filter arrangement and passes through the filter very rapidly. Filter efficiency is increased, permitting a reduction in filter size and reducing expensive treatment steps for the filter medium, such as siliconization to increase filter efficiency. Furthermore, the contact time with coagulation-active solid waste components is minimized. Due to the integration of the filter in the cover, the filter is not immersed in the temporarily stored blood. The filter retains practically no blood, thus greatly increasing the recovery of blood cells in the filter.

Figure 3:
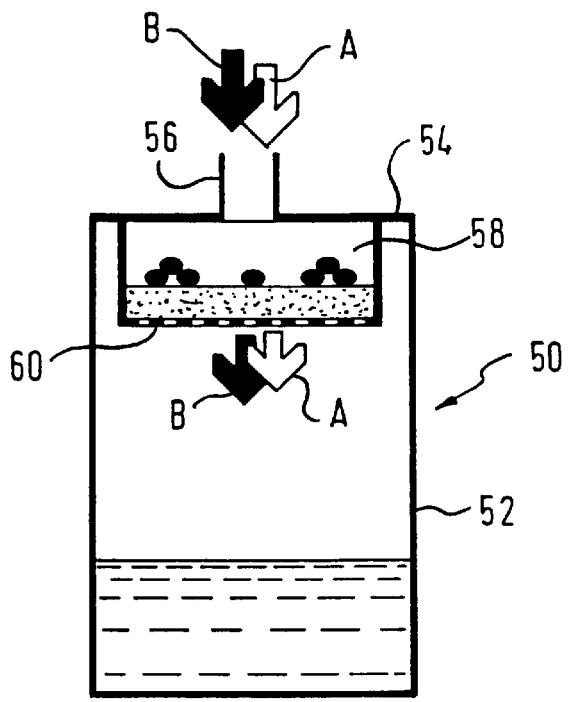
Figure 4:
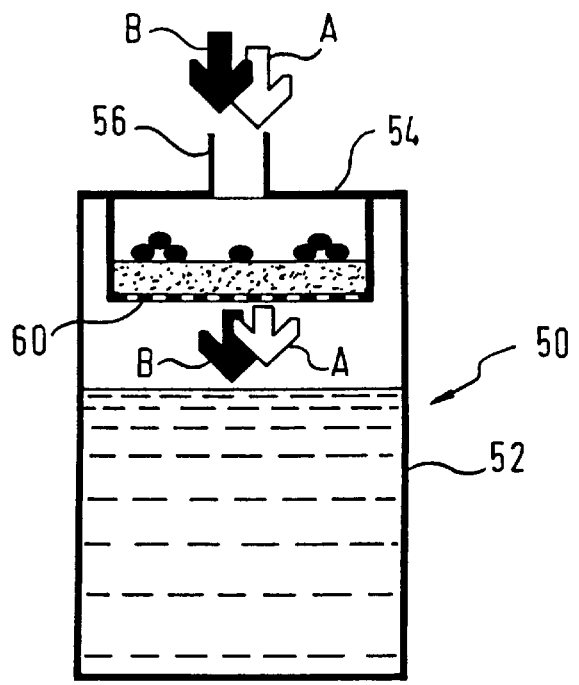

Additional details and advantages of this invention are explained in greater detail on the basis of one embodiment illustrated in the drawings, which show:

FIGS. 1 and 2: schematic diagrams of the blood collecting device according to the related art, as described previously;

FIG. 3: a schematic diagram of one embodiment of the blood collecting device according to this invention with a first filling level, and FIG. 4: the blood collecting device according to FIG. 3 with a second filling level.

The blood collecting device illustrated in FIGS. 3 and 4 shows only a schematic diagram. The basic function of the blood collecting device described in detail here corresponds to that according to European Patent No. 669,139 A as the preferred embodiment. For purposes of simplification in illustrating blood collecting device 50, FIGS. 3 and 4 show only bag 52, which is connected to a cover 54. This may also be a rigid container. A connection for a blood inlet tube 56 is provided in cover 54. In addition, a filter chamber 58 whose bottom is designed as a flat flexible filter element 60 is also integrated in cover 54, while the side walls are designed only as a mount. When using a flexible bag, the vacuum line must be arranged between the bag and the vacuum container; when using a rigid bag, it must be arranged in the cover. The vacuum line itself and the drain tube for the filtered blood mixture are not shown in detail here for reasons of simplicity.

It is clear from FIG. 3 that both the air intake A as well as the blood intake B are drawn into filter chamber 58. Both air A and blood B are drawn together through the flexible flat filter 60. This causes reservoir 52 to fill up with blood. In FIG. 3, the reservoir is only slightly full, whereas FIG. 4 shows it as full. Even when full, as shown in FIG. 4, the filter integrated into the cover 54 does not sit in the collected blood.

Greater differential pressures can be created with the blood collecting device according to this invention. Consequently, a higher flow rate and a smaller residual blood volume can be achieved in the filter. On the whole, a smaller filter can be used, and the blood remains in contact with the filter for a shorter period of time.

What is claimed is:

1. A blood collecting device comprising:
    a vacuum container;
    a cover for sealing the vacuum container, the cover having an opening therethrough;
    an inlet line connected to the cover, the inlet line being adapted to allow fluid to pass through the opening in the cover and into the vacuum container;
    a flexible blood filter spaced from the cover and the inlet line, and
    a filter chamber connected to the cover, the filter chamber including the blood filter.

2. The blood collecting device of claim 1, wherein the blood filter is substantially horizontally disposed.

3. The blood collecting device of claim 1 wherein the filter chamber includes a pair of opposing side walls and the filter bottom, the filter chamber extends downwardly from the cover and into the vacuum container.

4. The blood collecting device of claim 1 wherein the filter chamber includes a width and a height, the width of the filter chamber is greater than the height thereof.

5. The blood collecting device of claim 3 wherein the blood filter is secured between the opposing side walls of the filter chamber adjacent the bottom thereof.

* * * * *